(12) United States Patent
Tekulve et al.

(10) Patent No.: US 10,111,676 B2
(45) Date of Patent: Oct. 30, 2018

(54) LOOPED CLOT RETRIEVER WIRE

(71) Applicant: Cook Medical Technologies LLC, Bloomington, IN (US)

(72) Inventors: Kurt Tekulve, Ellettsville, IN (US); Tyler Turk, Greenwood, IN (US); Yunjuan Wu, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 508 days.

(21) Appl. No.: 14/267,497

(22) Filed: May 1, 2014

(65) Prior Publication Data

US 2014/0330302 A1 Nov. 6, 2014

Related U.S. Application Data

(60) Provisional application No. 61/818,137, filed on May 1, 2013.

(51) Int. Cl.
*A61M 29/00* (2006.01)
*A61B 17/221* (2006.01)

(52) U.S. Cl.
CPC .... *A61B 17/221* (2013.01); *A61B 2017/2212* (2013.01)

(58) Field of Classification Search
CPC .... A61F 2/01; A61F 2/06; A61F 2/013; A61F 2002/011; A61F 2002/016; A61F 2002/018; A61F 2230/006; A61F 2230/008; A61F 2230/0091; A61F 2002/015; A61B 17/221; A61B 2017/2212; A61B 17/22031; A61B 2017/2215; A61B 2017/2217; A61B 17/22; A61B 17/22012; A61B 17/32056; A61B 2017/22034; A61B 2017/22035; A61B 2017/22081; A61B 2017/320733
USPC .......................................... 606/200
See application file for complete search history.

(56) References Cited

U.S. PATENT DOCUMENTS

| | | | |
|---|---|---|---|
| 3,108,593 | A | 10/1963 | Glassman |
| 4,612,931 | A | 9/1986 | Dormia |
| 5,192,286 | A | 3/1993 | Phan et al. |
| 5,906,621 | A | 3/1999 | Secrest et al. |
| 6,099,534 | A * | 8/2000 | Bates ............... A61B 17/221 606/113 |
| 6,129,739 | A | 10/2000 | Khosravi |
| 6,402,771 | B1 | 6/2002 | Palmer et al. |
| 6,514,273 | B1 | 2/2003 | Voss et al. |
| 6,610,077 | B1 | 8/2003 | Hancock et al. |

(Continued)

*Primary Examiner* — Katrina Stransky
*Assistant Examiner* — Kankindi Rwego
(74) *Attorney, Agent, or Firm* — Brinks Gilson & Lione

(57) ABSTRACT

A clot retrieval system for removing clots from a body lumen. The clot retrieval system includes an elongated sheath and a wire assembly. The wire assembly is comprised of four wire segments, each biased to have a distally extending circumferential curve. Two wire segments are connected together at a proximal end and a distal end to form a first loop, and are connected to a shaft. Two other wire segments are connected together at a proximal end and a distal end to form a second loop and are connected to the first two wire segments. The second loop is covered with a membrane to catch clots. The wire assembly may be compacted by retracting it within the elongated sheath, or expanded by extending it from the elongated sheath.

18 Claims, 3 Drawing Sheets

(56) References Cited

U.S. PATENT DOCUMENTS

| | | | |
|---|---|---|---|
| 6,638,294 B1 | 10/2003 | Palmer | |
| 7,241,304 B2 | 7/2007 | Boyle et al. | |
| 7,252,675 B2 | 8/2007 | Denison et al. | |
| 7,316,692 B2 | 1/2008 | Huffmaster | |
| 7,331,976 B2 * | 2/2008 | McGuckin, Jr. | A61F 2/013 606/113 |
| 7,344,549 B2 | 3/2008 | Boyle et al. | |
| 7,582,100 B2 | 9/2009 | Johnson et al. | |
| 7,678,131 B2 | 3/2010 | Muller | |
| 7,976,560 B2 | 7/2011 | Denison et al. | |
| 2002/0072730 A1 * | 6/2002 | McGill | A61F 2/013 604/525 |
| 2002/0183783 A1 * | 12/2002 | Shadduck | A61F 2/013 606/200 |
| 2008/0147111 A1 * | 6/2008 | Johnson | A61F 2/01 606/200 |
| 2008/0234722 A1 * | 9/2008 | Bonnette | A61F 2/013 606/200 |
| 2008/0243170 A1 * | 10/2008 | Jenson | A61B 17/221 606/200 |
| 2009/0287193 A1 | 11/2009 | Desai et al. | |
| 2010/0268264 A1 * | 10/2010 | Bonnette | A61B 17/221 606/200 |
| 2013/0184739 A1 * | 7/2013 | Brady | A61B 17/221 606/200 |

\* cited by examiner

LOOPED CLOT RETRIEVER WIRE

FIELD

Embodiments of the present invention relate to medical devices and more particularly to devices and methods for retrieving clots in a body lumen.

BACKGROUND

Deep vein thrombosis (DVT) is a condition in which blood clots form in the deep veins of the body, commonly in the lower portion of the body. If a blood clot breaks free, it may travel to other parts of the body and cause significant damage. For instance, if a blood clot were to travel to the heart and lungs through the inferior vena cava, a pulmonary embolization could result, which can be fatal. If a blood clot is not dissolved or extracted, it will adhere to the wall of the vein over time and cause permanent damage to the vein.

Current methods of treating DVT include administering Heparin, an anticoagulant, to prevent further clots from forming and performing an intravenous procedure to remove the clot. In one procedure a physician sends a balloon catheter past a clot and then expands the balloon. The expanded balloon is then dragged to a location where the clot can be removed. It is easier to pass a catheter having a small profile past the clot compared to a catheter having a larger profile. However, a balloon catheter needs to have an inflation lumen for inflating the balloon, which limits how small the balloon catheter can be.

It would be beneficial to have a device and methods for retrieving a clot with a device having a lower profile than a balloon catheter.

SUMMARY

Embodiments of the invention include a clot retrieval system comprising an elongated sheath, a wire assembly, and a membrane. The elongated sheath has a lumen with an inner diameter. The wire assembly is disposed within the lumen and comprises a straight section and a curved section. A distal end of the straight section is connected to a proximal end of the curved section. The curved section is comprised of a first wire segment extending distally from the proximal end of the curved section and biased to curve in a first circumferential direction, a second wire extending distally from the proximal end of the curved section and biased to curve in a second circumferential direction opposite the first circumferential direction, a third wire segment extending distally from the first loop proximal end and biased to curve in the first circumferential direction, and a fourth wire segment extending distally from the first loop proximal end and biased to curve in the second circumferential direction. The first wire segment and the second wire segment form a first loop having a first loop proximal end and a first loop distal end. The first wire segment is connected to the second wire segment at the first loop proximal end and the first loop distal end. The third wire segment and fourth wire segment form a second loop having a second loop proximal end and a second loop distal end. The third wire segment is connected to the fourth wire segment at the second loop proximal end and the second loop distal end. The membrane is secured to third wire segment and the fourth wire segment bridging the second loop.

Another embodiment is directed to a looped wire assembly. The A looped wire assembly comprises a straight section, a first wire segment, a second wire segment, a third wire segment, a fourth wire segment, and a membrane. The straight section comprises a shaft having a shaft distal end and a shaft proximal end. The first wire segment is connected to the shaft distal end and extends distally and is biased to curve in a first circumferential direction. The second wire segment is connected to the shaft distal end and extends distally and is biased to curve in a second circumferential direction opposite the first circumferential direction. The first wire segment and second wire segment form a first loop having a first loop proximal end and a first loop distal end with the first wire segment being connected to the second wire segment at the first loop proximal end and the first loop distal end. The third wire segment is connected to the first loop proximal end and extends distally and is biased to curve in the first circumferential direction. The fourth wire segment is connected to the first loop proximal end and extends distally and is biased to curve in the second circumferential direction. The third wire segment and the fourth wire segment form a second loop having a second loop proximal end and a second loop distal end. The third wire segment is connected to the fourth wire segment at the second loop proximal end and at the second loop distal end. The membrane is secured to the third wire segment and the fourth wire segment bridging the second loop.

BRIEF DESCRIPTION OF THE DRAWINGS

To further clarify the above and other advantages and features of the one or more present inventions, reference to specific embodiments thereof are illustrated in the appended drawings. The drawings depict only typical embodiments and are therefore not to be considered limiting. One or more embodiments will be described and explained with additional specificity and detail through the use of the accompanying drawings in which.

The drawings are not necessarily to scale.

DETAILED DESCRIPTION

As used herein, "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" means A alone, B alone, C alone, A and B together, A and C together, B and C together, or A, B and C together.

Various embodiments of the present inventions are set forth in the attached figures and in the Detailed Description as provided herein and as embodied by the claims. It should be understood, however, that this Detailed Description does not contain all of the aspects and embodiments of the one or more present inventions, is not meant to be limiting or restrictive in any manner, and that the invention(s) as disclosed herein is/are and will be understood by those of ordinary skill in the art to encompass obvious improvements and modifications thereto.

Additional advantages of the present invention will become readily apparent from the following discussion, particularly when taken together with the accompanying drawings.

In the following discussion, the terms "distal" and "proximal" will be used to describe the opposing axial ends of the inventive balloon catheter, as well as the axial ends of various component features. The term "distal" is used in its conventional sense to refer to the end of the apparatus (or component thereof) that is furthest from the operator during use of the apparatus. The term "proximal" is used in its conventional sense to refer to the end of the apparatus (or component thereof) that is closest to the operator during use. For example, a catheter may have a distal end and a proximal end, with the proximal end designating the end closest to the operator during an operation, such as a handle, and the distal end designating an opposite end of the catheter, such as the treatment tip. Similarly, the term "distally" refers to a direction that is generally away from the operator along the apparatus during use and the term "proximally" refers to a direction that is generally toward the operator along the apparatus.

Figure 1:
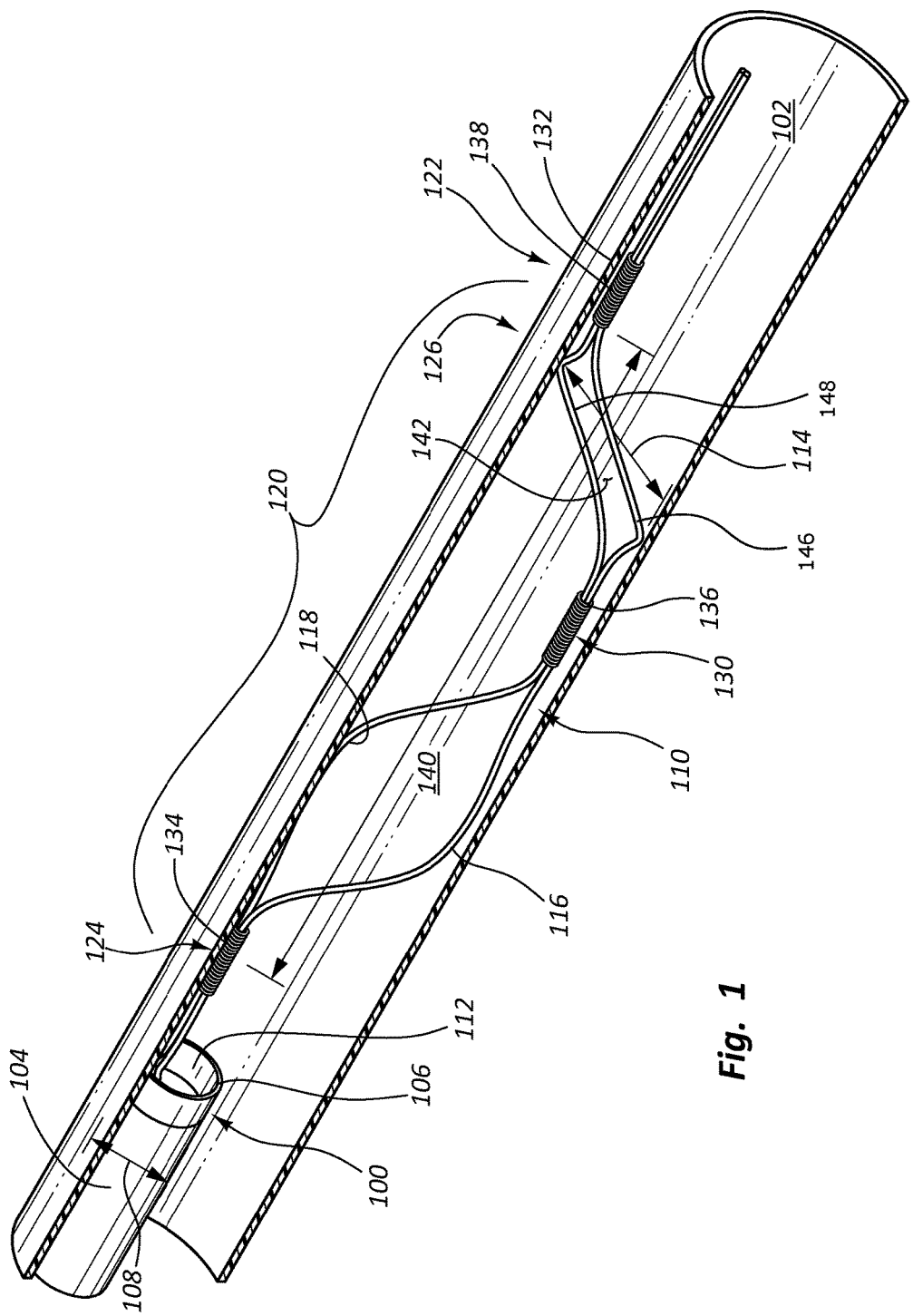
FIG. 1 is a perspective view of a body lumen having a clot retrieval system disposed within it.

FIG. 1 illustrates a distal end of a clot retrieval system 100 within a cut away body lumen 102, such as a blood vessel. The clot retrieval system 100 comprises an elongated sheath 104 having a longitudinal lumen 106. The elongated sheath 104 has outside diameter 108 sized to be passed within the body lumen 102. The longitudinal lumen 106 of the elongated sheath 104 is sized to house a wire assembly 110 in a collapsed configuration (not shown). The longitudinal lumen 106 has an inside diameter 112 that is less than an outside diameter 114 of the wire assembly 110 in an expanded configuration shown in FIG. 1.

The clot retrieval system 100 further comprises the wire assembly 110 disposed within the longitudinal lumen 106. The wire assembly 110 is not connected to the elongated sheath 104 such that the wire assembly 110 is able to move within the longitudinal lumen 106. The wire assembly 110 has a straight section disposed proximal to a curved section 120, which is disposed proximate a distal end of the wire assembly 110. The straight section may comprise a shaft of a super elastic material such as a nickel titanium alloy. A distal end of the straight section is connected to a proximal end 124 of the curved section 120. The curved section 120 of the wire assembly 110 is comprised of a first wire segment 116, a second wire segment 118, a third wire segment 146, and a fourth wire segment 148.

The first wire segment 116 and second wire segment 118 are connected at a distal end 130 of the first wire segment 116 and of the second wire segment 118, and are also connected at a proximal end 124 of the first wire segment 116 and the second wire segment 118. The first wire segment 116 extends longitudinally and is biased to curve in a circumferential direction for a half turn from the proximal end 124 to the distal end 126. The second wire segment 118 segment extends longitudinally and is biased to curve in a circumferential direction opposite the first wire segment 116 for a half turn from the proximal end 124 to the distal end 126. In one embodiment, the first wire segment 116 may comprise a right handed helix and the second wire segment 118 may comprise a left handed helix. When viewed axially, the first wire segment 116 and the second wire segment 118 form a circular shape having an outside diameter 114 greater than the inside diameter 112 of the longitudinal lumen 106. The first wire segment 116 and the second wire segment 118 together form a first loop 140 between the proximal end 124 and the distal end 130.

The third wire segment 146 and fourth wire segment 148 are connected at a distal end 122 of the third wire segment 146 and of the fourth wire segment 148, and are also connected at a proximal end of the third wire segment 146 and the fourth wire segment 148. The distal end 130 of the first wire segment 116 and the second wire segment 118 is connected to the proximal end of the third wire segment 146 and the fourth wire segment 148. The third wire segment 146 extends longitudinally and is biased to curve in a circumferential direction for a half turn from the proximal end to the distal end 122. The fourth wire segment 118 segment extends longitudinally and is biased to curve in a circumferential direction opposite the third wire for a half turn from the proximal end to the distal end 122. In one embodiment, the third wire segment 146 may comprise a right handed helix and the fourth wire segment 148 may comprise a left handed helix. When viewed axially, the third wire segment 146 and the fourth wire segment 148 form a circular shape having an outside diameter 114. The third wire segment 146 and the fourth wire segment 148 together form a second loop 142 between their distal end and their proximal end 122.

Each of the wire segments may be connected to another wire segment through the use of fasteners. The fasteners may comprise fasteners generally known in the art for coupling wires such as coiled wire segments, bands, welding, soldering, over molding, and adhesives. In some embodiments the wire segments may be segments of a common wire. For example, the first wire segment 116 and the third wire segment 146 may be segments of a single wire, connected together by being a single wire. Similarly a single wire may comprise the first wire segment 116, the second wire segment 118, the third wire segment 146, and the fourth wire segment 148. The wire segments may be comprised of material having shape memory and high elasticity, such as a nickel titanium alloy.

The first wire may be connected to the second wire segment 118 at the proximal end by a first fastener 134. The first fastener 134 inhibits the first wire 116 from moving longitudinally and laterally relative to the second wire segment 118 such that they move as a single wire assembly 110. A second fastener 136 may connect the first wire 116 to the second wire segment 118 at the distal end of the first and second wire segment 118. The second fastener 136 inhibits the first wire from moving longitudinally and laterally relative to the second wire segment 118 near the second fastener. The second fastener 136 may also connect the distal end of the first wire section and second wire segment 118 section to the proximal end of the third wire section and the fourth wire section.

A third fastener 138 may connect the third wire 116 to the fourth wire segment 118 at a distal end of the curved section 120. The third fastener 138 inhibits the third wire segment 116 from moving longitudinally and laterally relative to the fourth wire segment 118 near the third fastener.

Figure 2:
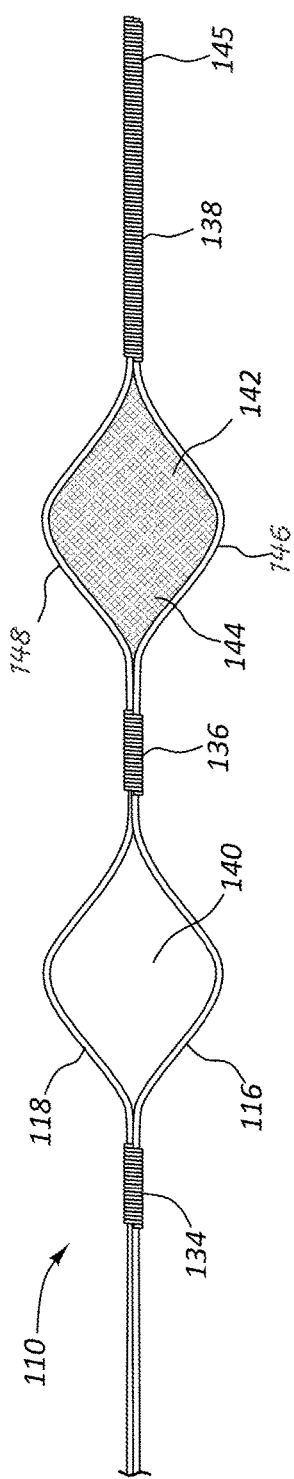
FIG. 2 is a top view of a wire assembly used in FIG. 1.
Figure 3:
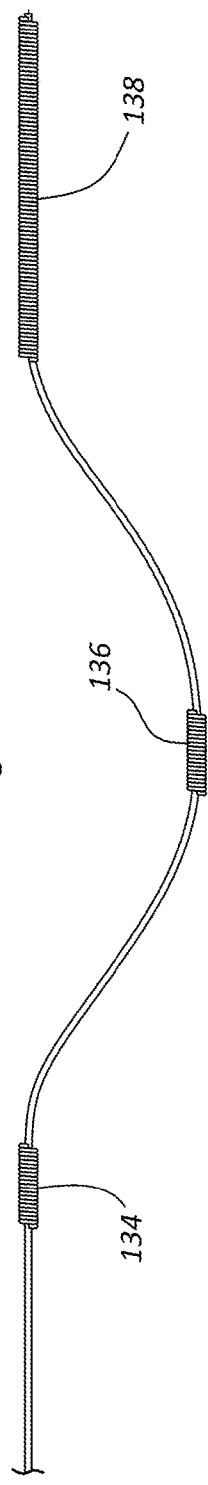
FIG. 3 is a side view of the wire assembly of FIG. 2.

FIG. 2 illustrates the distal end of the wire assembly 110 removed from the elongated sheath 104 to better illustrate the first loop 140 and the second loop 142. FIG. 3 illustrates the distal end of the wire assembly 110 viewed from the side of FIG. 2.

Figure 5:
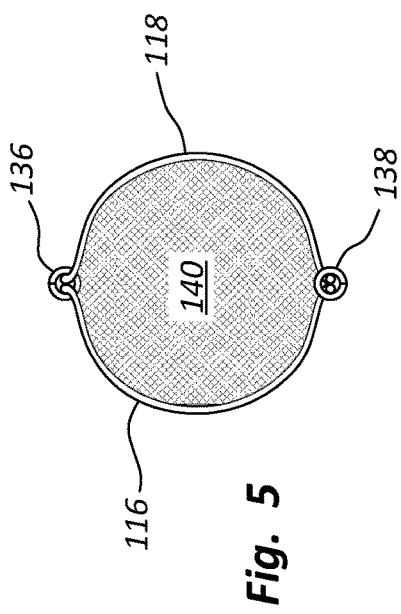
FIG. 5 is a head on view of the wire assembly of FIG. 2.

A membrane 144 is secured to the third wire segment 146 and the fourth wire segment 148. The membrane 144 bridges the second loop 142, or gap between the third wire segment 146 and the fourth wire segment 118. Because the third wire segment 146 and the fourth wire segment 148 are biased in a circumferential shape, the membrane 144 is substantially round when viewed axially. This is best shown in FIG. 5 which illustrates a head on view of the wire assembly 110.

The second fastener 136 is shown at the top of the round cross section, and the third fastener 138 is shown at the bottom of the round cross section with the membrane 144 spanning the second loop 142 between the third wire segment 146 and the fourth wire segment 148.

In some embodiments, the membrane 144 may comprise a thin sheet of elastic polymer, such as a thin elastomeric film or a silicone polymer film. The membrane 114 may be stretched across the third wire segment 146 and the fourth wire segment 148, or it may be loosely attached to have some sag between the third wire segment 146 and the fourth wire segment 148. The loose attachment may allow the membrane 144 to sag creating a pocket-like structure to collect clot material.

Figure 4:
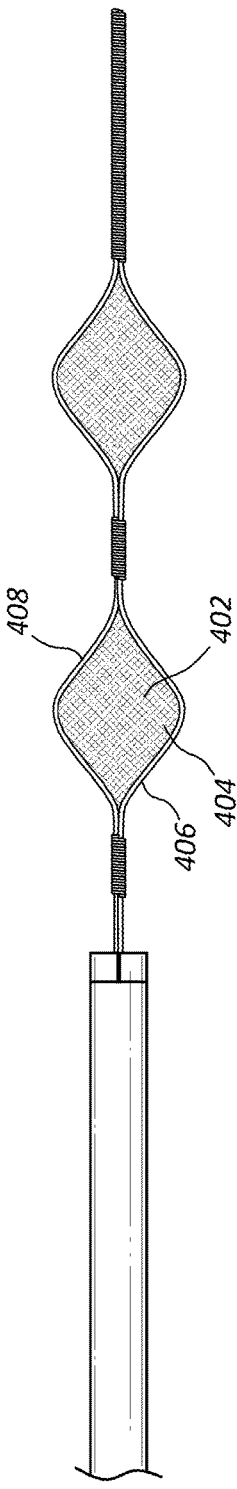
FIG. 4 is a top view of another embodiment of a wire assembly.

FIG. 4 illustrates an alternative embodiment of a wire assembly 400 in which a mesh 402 covers the first loop 404. The mesh 402 is secured to first wire segment 406 and the second wire segment 408 and spans the first loop 404. The mesh 402 may be comprised of a plurality of filaments, which may comprise a material such as a nickel titanium alloy, fivers, etc. The mesh 402 may be used to break up a clot into smaller pieces during use.

The wire assembly 110 shown in FIG. 2 has a flexible tip 145 disposed at the distal end of the wire assembly 110. The flexible tip 145 is formed by winding a flexible wire in a tight helix. The flexible tip 145 may be combined with the third fastener 138 to fasten the first wire segment 116 to the second wire 118. In other embodiments a conical tip may be formed over the first wire segment 116 and the second wire 118 distal to the second loop 142. The conical tip may enable the wires 116, 118 to act as a dilator enabling them to pass through smaller body lumens. In other embodiments the tip may be angled, straight, floppy, a J-tip, or any other tip type as known in the art. The flexible tip 145 may be ground to create a softer, floppier tip.

Figure 6:
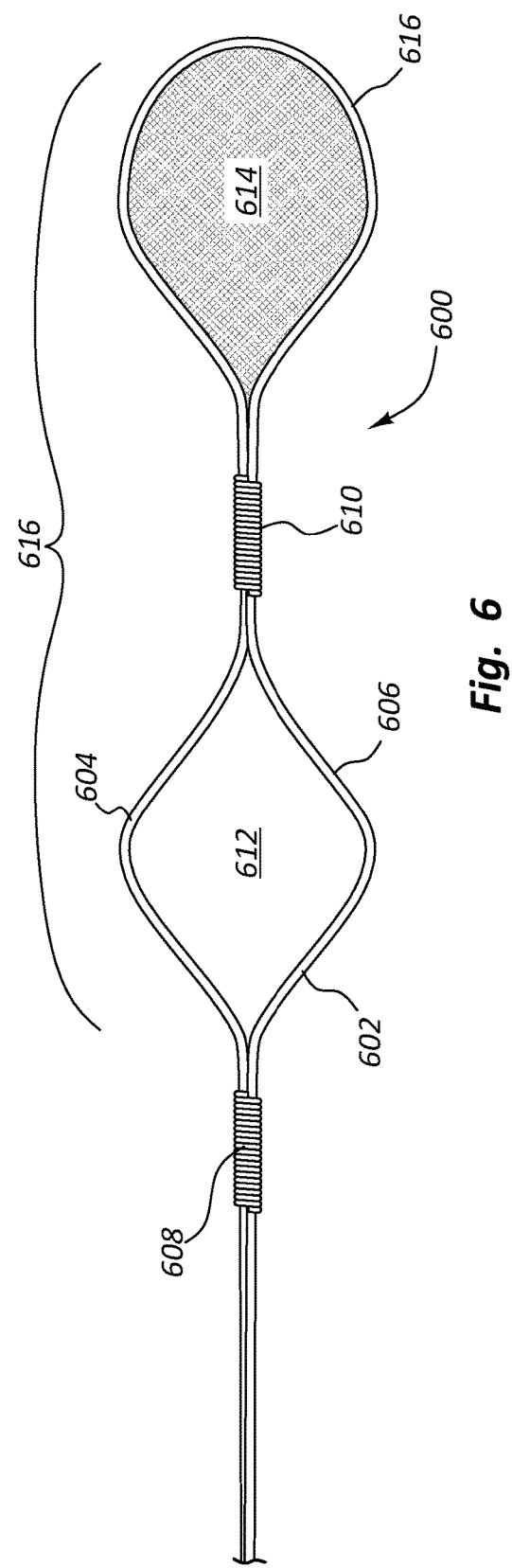
FIG. 6 is a top view of another embodiment of a wire assembly.

FIG. 6 illustrates an alternative embodiment of a wire assembly 600. This embodiment comprises a wire 602 that loops back on itself to form a first wire segment 116, a second wire segment 118, and a third wire segment 146. The first wire segment 116 and the second wire segment 118 are connected at their proximal en and their distal end. The first wire segment 116 extends distally and curves in a circumferential direction for a half turn. The second wire segment 118 extends distally and curves in a circumferential direction opposite the first wire segment 116. The third wire segment 146 has a first end and a second end that are connected to the distal end of the first wire segment 116 and the second wire segment 118 to form a first loop. The third wire segment 146 extends distally from the first end while curving circumferentially for half a turn and then extends proximally while continuing to curve circumferentially for another half turn to the second end to form a second loop.

The first wire segment 116 may be connected to the second wire segment 118 by a first fastener 608 at a proximal end of a curved section 608. A second fastener 610 may connect the first wire segment 116 to the second wire segment 118 at a distal end of the first wire segment 116 and the second wire segment 118. The second fastener 610 may also connect the first end and second end of the third wire segment 146 to the distal end of the first wire segment 116 and the second wire segment 118. A membrane 616 is attached to the third wire segment 146 to span the second loop 614.

Embodiments of the invention include a method of using the looped clot retriever to retrieve a clot. The procedure will be described in relation to FIG. 1. Initially, a user will obtain a clot retrieval system, such as the clot retrieval system 100 of FIG. 1. The clot retrieval system 100 is inserted into a patient's vascular system with the wire assembly 110 disposed in the longitudinal lumen 106 of the elongated sheath 104. Because the inside diameter 112 of the lumen 106 is smaller than the biased spiral diameter of the first wire segment 116 and the second wire, the wire assembly 110 is compacted radially while in the elongated sheath 104 with the inner wall of the elongated sheath 104 providing a constraint to the wire assembly 110 so it does not open. In this compacted configuration, the distal end of the clot retrieval system is 100 is guided to a location just past a clot. The wire assembly 110 is advanced relative to the elongated sheath 104, removing the radial constraint of the elongated sheath 104 allowing the first wire segment 116 and the second wire to expand to their biased configuration. Advancing the wire assembly 110 relative to the elongated sheath 104 includes the elongated sheath 104 moving proximally while the wire assembly 110 is held in place longitudinally. The clot retrieval system 100 may then be moved proximally to retrieve the clot. The first loop scrapes the walls of the body lumen, loosening the clot, while the second loop catches the clot on the membrane. In embodiments in which a loose membrane is used, the clot may be caught in a pocket formed by the membrane. In some embodiments, the wire mesh on the first loop breaks up the clot as it is forced through the mesh.

Embodiments of the invention have been primarily described in relation to the clot retrieval system of FIG. 1. It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

What is claimed:
1. A clot retrieval system comprising:
an elongated sheath having a lumen disposed therein, the lumen having an inner diameter;
a wire assembly disposed within the elongated sheath, the wire assembly comprising a straight section and a curved section, a distal end of the straight section connected to a proximal end of the curved section, the curved section being comprised of a first wire segment extending distally from the proximal end of the curved section and biased to curve in a first circumferential direction, a second wire segment extending distally from the proximal end of the curved section and biased to curve in a second circumferential direction opposite the first circumferential direction, the first wire segment and second wire segment forming a first loop having a first loop proximal end and a first loop distal end, the first wire segment being connected to the second wire segment at the first loop proximal end and the first loop distal end to prevent the first wire segment from moving relative to the second wire segment, a third wire segment extending distally from the first loop distal end and biased to curve in the first circumferential direction, a fourth wire segment extending distally from the first loop distal end and biased to curve in the second circumferential direction, the third wire segment and fourth wire segment forming a second loop having a second loop proximal end and a second loop distal end, the third wire segment being connected to the fourth wire segment at the second loop proximal end and the second loop distal end to prevent the third wire segment from moving relative to the fourth wire segment, wherein the second loop proximal end is connected to and extends from the first loop distal end, and a side view of the first loop and the second loop is arc-shaped;

an elastic membrane secured to the third wire segment and the fourth wire segment and not secured to the first wire segment or second wire segment, the membrane bridging the second loop and configured to collect clot material; and a mesh comprised of a plurality of woven filaments secured to the first wire segment and the second wire segment and not secured to the third wire segment or the fourth wire segment, the mesh bridging the first loop and configured to break up a clot into smaller pieces;

wherein the curved section of the wire assembly is disposed on only one side of an axis defined by the straight section of the wire assembly.

2. The clot retrieval system of claim 1 wherein the elastic membrane comprises a polymer film.

3. The clot retrieval system of claim 1 wherein the mesh comprises a plurality of woven nickel titanium strands.

4. The clot retrieval system of claim 1 further wherein the wire assembly further comprises a distal section connected to the distal end of the second loop, the distal section comprising a helical wire.

5. The clot retrieval system of claim 1 wherein the first wire segment, the second wire segment, the third wire segment, and the fourth wire segment comprise a single wire.

6. The clot retrieval system of claim 1 wherein the curved section has only two loops.

7. The clot retrieval system of claim 1, further comprising a first fastener connecting the first wire segment and the second wire segment at the first loop proximal end, a second fastener connecting the first wire segment and the second wire segment as the first loop distal end and the third wire segment and the fourth wire segment at the second loop proximal end, and a third fastener connecting the third wire segment and the fourth wire segment at the second loop distal end.

8. The clot retrieval system of claim 7, wherein the first fastener, second fastener, and third fastener are selected from the group consisting of a solder joint, a weld, a band, and a coil.

9. A looped wire assembly comprising:

a straight section comprising a shaft having a shaft distal end and a shaft proximal end;

a first wire segment connected to the shaft distal end and extending distally and biased to curve in a first circumferential direction;

a second wire segment connected to the shaft distal end and extending distally and biased to curve in a second circumferential direction opposite the first circumferential direction, the first wire segment and second wire segment forming a first loop having a first loop proximal end and a first loop distal end, the first wire segment being connected to the second wire segment at the first loop proximal end and the first loop distal end to prevent the first wire segment from moving relative to the second wire segment;

a third wire segment connected to the first loop distal end and extending distally and biased to curve in the first circumferential direction;

a fourth wire segment connected to the first loop distal end and extending distally and biased to curve in the second circumferential direction, the third wire segment and the fourth wire segment forming a second loop having a second loop proximal end and a second loop distal end, the third wire segment being connected to the fourth wire segment at the second loop proximal end and the second loop distal end to prevent the third wire segment from moving relative to the fourth wire segment;

a flexible membrane secured to the third wire segment and the fourth wire segment and not secured to the first wire segment or second wire segment, the membrane bridging the second loop and configured to collect clot material; and a mesh comprised of a plurality of woven filaments secured to the first wire segment and the second wire segment and not secured to the third wire segment or the fourth wire segment, the mesh bridging the first loop and configured to break up a clot into smaller pieces;

wherein the first loop and the second loop are disposed on only one side of an axis defined by the straight section, the second loop proximal end is connected to and extends from the first loop distal end, and a side view of the first loop and the second loop is arc-shaped.

10. The looped wire assembly of claim 9 wherein the first wire segment, the second wire segment, the third wire segment, and the fourth wire segment are segments of a single looped wire.

11. The looped wire assembly of claim 9 wherein the first wire segment and the third wire segment comprise a first wire, and the second wire segment and the fourth wire segment comprise a second wire.

12. The looped wire assembly of claim 9 wherein the mesh comprises a plurality of interwoven strands of a nickel titanium alloy.

13. The looped wire assembly of claim 9 further comprising a distal section comprising a distally extending shaft connected to the second loop distal end.

14. The looped wire assembly of claim 13 further wherein the distal section is encapsulated in a soft material.

15. The looped wire assembly of claim 14 wherein the distal section comprises a helical wire.

16. The looped wire assembly of claim 9 further comprising a first fastener connecting the shaft to the first and second wire segment.

17. The looped wire assembly of claim 16 further comprising a second fastener connecting the first wire segment to the second wire segment and the third wire segment to the fourth wire segment.

18. The looped wire assembly of claim 16 wherein the first fastener is selected from the group consisting of a solder joint, a weld, a band, and a coil.

* * * * *